United States Patent [19]

Kraemer et al.

[11] 4,039,413

[45] Aug. 2, 1977

[54] METHOD OF BONDING A POLYPEPTIDE TO A MACROMOLECULAR POLYMERIC CARRIER BY IRRADIATION WITH LIGHT

[75] Inventors: Dieter Kraemer, Mainz; Klaus Lehmann, Rossdorf, Darmstadt; Hermann Plainer, Darmstadt, all of Germany

[73] Assignee: Rohm GmbH, Darmstadt, Germany

[21] Appl. No.: 426,317

[22] Filed: Dec. 19, 1973

[30] Foreign Application Priority Data

Dec. 23, 1972 Germany .............................. 2263289

[51] Int. Cl.² .......................... C08L 1/00; C08L 3/00
[52] U.S. Cl. ................................. 204/159.12; 195/63; 195/68; 204/160.1; 260/8; 260/17 R; 260/17.4 R; 260/17.4 CL; 260/17.4 ST; 260/112 R; 260/112.7; 424/78
[58] Field of Search ....................... 204/159.12, 160.1; 260/8, 112 R; 195/63, 68

[56] References Cited

U.S. PATENT DOCUMENTS

| | | | |
|---|---|---|---|
| 3,453,194 | 7/1969 | Bennett et al. | 204/159.12 |
| 3,764,477 | 10/1973 | Lehmann et al. | 195/63 |
| 3,775,253 | 11/1973 | Dieter et al. | 195/63 |
| 3,808,113 | 4/1974 | Okamura et al. | 204/159.12 |
| 3,871,964 | 3/1975 | Hüper et al. | 195/63 |
| 3,910,825 | 10/1975 | Hüper et al. | 195/116 |
| 3,969,287 | 7/1976 | Jaworek et al. | 260/8 |

*Primary Examiner*—Richard B. Turer
*Attorney, Agent, or Firm*—Curtis, Morris & Safford

[57] ABSTRACT

Methods for bonding a polypeptide to a macro-molecular carrier compound by irradiating an aqueous solution of the polypeptide, in the absence of oxygen and in the presence of said carrier compound, with ultraviolet light in the optional presence of a photosensitizer or with visible light in the presence of a photosensitizer and an organic peroxide.

9 Claims, No Drawings

METHOD OF BONDING A POLYPEPTIDE TO A MACROMOLECULAR POLYMERIC CARRIER BY IRRADIATION WITH LIGHT

The present invention relates to a method for bonding polypeptides to a carrier and relates more in particular to a photochemical method for making such carrier-bound polypeptides.

The use of carrier-bound protein bodies has acquired ever-increasing significance in science and technology since such bodies provide the simplest and safest way to separate active substances and substrates after their combination. For this reason, numerous development laboratories have set as a goal the development of carriers for proteinaceous active substances, which carriers will accept proteins from aqueous solution as quickly and as completely as possible with the greatest possible retention of their biological activity and which will not again release the active substances when they are used. After batchwise action on a substrate, the carrier-bound active substance should be quickly separable from the substrate solution by filtration with as little residue as possible and, in a continuous operation, discharge of the material should permit a high throughput velocity. Now, after the first preparations containing an active substance, for example an enzyme, bound to a synthetic or pre-treated natural macromolecule were obtained and were found to be quite imperfect, products which are the result of years' long development work are available which have a high content of active material and a good filterability.

Certain disadvantages of these products were heretofore considered in principle to be unavoidable. These carrier substances contain groups which are reactive with polypeptides, especially with terminal and side-chain amino groups, and are able to react therewith to form an amide group. These groups, such as carboxylic acid anhydride, carboxylic acid chloride, or phenyl ester groups, are water-sensitive and are hydrolyzed to a considerable degree before they enter into a reaction with protein bodies. The carboxyl groups which are formed by hydrolysis have negative charges which can interfere on later reaction with also negatively-charged substrate molecules and, further, considerably alter the matrix properties of the carrier. Other functional groups, whose hydrolysis produces amino or hydroxy groups instead of carboxyl groups, react so slowly that either extraordinarily long reaction times are required for the bonding of proteins or reaction conditions which are harmful to biological activity are required. Further, the conversion of the basic amino groups of a protein body, which groups are often functionally necessary, into non-basic amide groups often causes a loss of biological activity so that only that portion of the bound material remains active which, more or less fortuitously, has not been converted into a non-functionally important amide group by the bonding.

An object of the present invention is the bonding of polypeptides to carrier substances under conditions which preserve activity and wherein, particularly, low temperatures and such pH values shall prevail that the biological activity of the polypeptide is not influenced. No new polar — or even ionic — groups should form in the carrier by hydrolysis or other side reactions during or after the bonding process, so that the matrix structure of the carrier substance remains unchanged. Further, it is required of the carrier/polypeptide combinations that the biological activity of the bound polypeptide should be retained as much as possible and that the combinations should, according to the intended use, be water-soluble or water-swellable and, in the latter instance, should also be easily filterable and washable.

It has now been found that the photochemical bonding of polypeptides onto carrier substances satisfies these numerous requirements.

It is known from the work of D. Elad and coworkers [cf. D. Elad et al., J. Am. Chem. Soc., 93, 967 – 971 (1971)] at the Weizmann Institute in Rehovoth, Israel, that toluene or lower olefins such as 1-butene can be bonded to glycine or glycine-containing polypeptides by photochemical reactions. In the reaction, the glycine units are converted into those of phenyl alanine or norleucine. In a typical reaction of this type [cf. J. Sperling, J. Am. Chem. Soc., 91, 5389 – 90 (1969)], a polypeptide comprising 90 percent of D,L-alanine and 10 percent of glycine and having a molecule weight of 4800 is reacted with 1-butene or toluene in a solution of water, t-butyl alcohol, and acetone (as a sensitizing agent) by exposure to ultraviolet light for 72 hours at room temperature. Polypeptides are obtained which are partly soluble and partly insoluble and which contain from 0.5 – 1 percent or norleucine units or from 2 – 3 percent of phenylalanine units. This corresponds to a transformation of the glycine units present of from 5 – 10 percent in the case of butene and from 20 – 30 percent in the case of toluene. Elad [European Biophysical Congress Proceedings, II, 75 – 78 (1971)] further found a detrimental influence on biological activity by photochemical reactions. Thus, by reaction with toluene or butene, lysozyme is completely inactivated and ribonuclease is inactivated to an extent of 90 percent.

A multiplicity of other photochemical reactions are known from numerous investigations carried out by different research groups. It can be said, in summarizing, that these reactions occur without specificity and with low yields.

Thus, it was not at all obvious to employ photochemical reactions for the bonding of polypeptides to carrier substances since it is a general experience that reactions between macromolecules occur less readily than do reactions between macromolecules and low molecular weight compounds. Thus, for the bonding of polypeptides to carrier substances, heretofore only those reactions which take place quantitatively in the low molecular weight region have been used. However, in this instance the bonding of only small amounts of polypeptides has been achieved. For this reason, a photochemical addition to bond polypeptides to carrier substances first appeared hopeless. In addition, it was to be expected that every bonding between polypeptides and carriers would involve only a minor retention of biological activity. Thus, for instance, the activity of trypsin is reduced to a fraction of its original activity by acylation with polyacrylic acid derivatives whereas, in contrast, acetylation influences the activity of trypsin only insignificantly. The same observation is true also of insulin and many other biologically active proteins.

It was, thus, completely surprising that polypeptides could, by a photochemical technique, be bound quantitatively, with extensive retention of their biological activity and under protective conditions, to carrier substances of the most different kinds. The fact that the photochemical reaction is not fundamentally restricted to particular reactive groups to a large extent permits a choice of carrier substances depending on the requirements of the ultimate use. Thus, water-soluble carriers can be used as well as water-insoluble swellable gels or pearl polymers or, even, inorganic substances modified with organic compounds.

The reaction of polypeptides with macromolecular carrier substances should, in every case, permit the formation of one covalent bond between one single reactive group of the polypeptide with one single reactive group of the carrier molecule. A quantitative reaction of all reactive groups of both components is, thus, not at all necessary. Nevertheless, if in many cases a lower yield is obtained in the reaction of polypeptides with macromolecules than for analogous reactions with lower molecular weight compounds, it must be remembered to what considerable extent reactions between macromolecules are disadvantaged in comparison with reactions between lower molecular weight compounds. Thus, it was not foreseeable that just here, in a photochemical reaction, the reaction of macromolecular partners proceeds more completely than does the reaction of polypeptides with lower molecular weight compounds.

Although the present invention should not be bound to any particular theory, this surprising effect can be explained by the fact that in photochemical reactions, to the extent that their mechanism has heretofore been known, predominantly hydrophobic molecular portions react with one another, for example the methylene group of the glycine residue with butene or toluene. Since polypeptides, as an entirety, are sooner to be viewed as hydrophilic than as hydrophobic and are obtainable only in aqueous or other strongly polar reaction media, it may be that the photochemically reactive non-polar groups are strongly screened by the strongly-solvated polar groups of the polypeptide and are only poorly accessible to small hydrophobic molecules. In contrast, the carrier substances used according to the present invention are, as a rule, hydrophilic so that there is an exchange effect and mutual arrangement with the hydrophilic groups of the polypeptide. Because of this effect, the hydrophobic, photochemically-active, groups of both macromolecules are necessarily brought into proximity and their reaction is facilitated.

Thus, one feature of the present invention is a method for the preparation of carrier-bound polypeptides in which an aqueous solution of a polypeptide, in the presence of a non-peptide-like macromolecular carrier compound and suitably in the further presence of a known photosensitizer is irradiated in the absence of oxygen with ultraviolet light or is irradiated with visible light in the additional presence of an organic peroxide.

The term "polypeptide" is to be broadly interpreted in the present invention. The term encompasses not only water-soluble natural protein bodies such as enzymes, antibodies, hormones having a protein structure, and inhibitors, but also natural or synthetic polypeptides, including peptides comprising at least four amino acid groups, or compounds which are only partially of a peptide-like structure, e.g. penicillins. In addition, substances which have no peptide structure can be reacted with oligomeric peptides and can be bound to carrier molecules by way of these groups. In each case, the polypeptides suitably includes at least one glycyl group therein since this group has proved particularly adaptable to photochemical bonding.

According to the present invention, the term "carrier" is to be employed in a more comprehensive sense that has been heretofore understood in the biochemical literature. The term encompasses not only insoluble solids, but also water-soluble compounds which function as a vehicle for the bound polypeptide and can, for example, influence the transport of the polypeptide to particular destinations in a biological system, its permeability through boundary layers or membranes, its distribution between different phases, and the like.

Because of the low specificity of the photochemical reaction, a great variety of non-peptide-like compounds come into consideration as macromolecular carrier substances. In the majority of cases, natural or synthetic organic polymers are involved. Nevertheless, inorganic carriers can also be employed to the extent that they are sufficiently transparent to the activating radiation, have a sufficient internal surface area, and have, on this surface photochemically activatable organic groups. As examples of inorganic carriers of this type can be mentioned porous glass, swellable silicates — particularly clay minerals —, or highly dispersed silicic acid, which are modified with siloxanes containing alkenyl-, toluyl-, or other groups capable of photochemical addition.

The organic carrier substances used in the majority of cases have a molecular weight greater than 1000, preferably more than 10000. They can be water-soluble, non-cross-linked, materials but for most uses water-insoluble substances are employed. Among these, preferably such which predominantly comprise hydrophilic monomer units and are water-insoluble only because of their cross-linked structure, are preferred. For carrier substances of this kind, it is well known that no molecular weights can be given. The cross-linking is preferably so slight that the materials are swellable in water. By swelling to at least twice their dry volume, a large "interior surface" is already made accessible for the bonding of polypeptides. Nevertheless, in order to permit penetration by very large protein molecules and, after their photochemical bonding, also to permit the inward and outward diffusion of large substrate molecules, a strong swellability in water, for example to a five-fold volume, preferably to a ten- to 200-fold volume of the dry volume, is advantageous.

When cross-linked or non-cross-linked carrier substances which do not swell in a solution of the polypeptide, or swell to less than twice their dry volume, are employed, they should be present in the form of the most finely-divided particles, for example latex particles having a maximum diameter of one micron, in order to permit the bonding of a sufficient number of polypeptide molecules. Polypeptides can be photochemically bonded to a variety of known natural or synthetic polymer latices. Such loaded latex particles can then be employed, like blood corpuscles, as carriers for biologically active substances.

Among the water-soluble or water-swellable carrier substances which are basically suitable for use in the process of the present invention, those characterized by a high photochemical reactability are formed completely or partially from highly hydrophilic monomer units tending toward free radical formation. This is true for macromolecular compounds having carboxylic acid amide, carboxylic acid ester, lactone, semi-acetal, and cyclic ether groups. The homopolymers and copolymers of acrylamide or of vinyl pyrrolidone, as well as polysaccharides, have proved to be very reactive. Among the preferred polysaccharides are those natural and synthetic materials which have heretofore proved in biochemistry to be very useful carrier materials, such as sepharose, polydextran gels, agarose gels, cellulose in the form of powders, fibers, webs (e.g., filter paper), as regenerated films, or the like. The hydroxyl groups of the polysaccharide can, for example, be partially etherified or esterified in order to decrease biological degradability. Characteristically, these materials include in their structure a group of the formula

wherein all unsatisfied valences in the formula are, in the compound, attached to carbon atoms. In the case of the polysaccharides, the free radical reaction probably attacks the C-H bond adjoining the ring-oxygen atom, whereupon a hydrogen atom is split off and a carbon radical is formed [cf. I. Rosenthal et al., Tetrahedron Letters 23, 3193 – 3204 (1967)].

Analogously, in polymers containing carbonamide groups, a C-H bond in the α-position to the carbonamide group is cleaved with formation of a C-radical [cf. the article by I. Rosenthal in "The Chemistry of Amides", S. Patai and J. Zabricky, page 303, Interscience Publishers, New York (1970)]. Homopolymers and copolymers of methacrylamide, which have no α-carbon hydrogen, are therefore less reactive and less preferred than are homopolymers and copolymers of acrylamide or vinyl pyrrolidone. Since these monomer units are at the same time strongly hydrophilic, the presence of other further comonomers does not decisively influence hydrophilicity and photochemical reactability although, basically, hydrophilic comonomers are preferred. These include methacrylamide; acrylic acid and methacrylic acid as well as their water-soluble salts; vinyl pyrrolidone; hydroxy alkyl esters of acrylic acid or methacrylic acid such as hydroxyethyl acrylate, 2-hydroxypropyl acrylate, butane diol-1,2-acrylate, butane diol-1,4-acrylate, or the corresponding methacrylates; or aminoalkyl esters or aminoalkyl amides of acrylic acid or methacrylic acid as well as their salts or quaternization products, such as dimethylaminoethyl methacrylate or its hydrochlorides or hydroacetates, and methacryloxyethyl-trimethyl ammonium chloride.

The polymers can be cross-linked by the presence of small amounts of comonomers having two or more polymerizable double bonds, such as divinyl benzene, glycol-diacrylate or -dimethacrylate, or triallyl cyanurate.

In addition to the aforementioned hydrophilic or water-soluble monomers, water-insoluble monomers can be present in the structure of the carrier molecules even if the latter are to be water-soluble or readily swellable by water. The carrier substances are, in this case, water-soluble or easily swellable if they are a vinyl polymer that — optionally in the addition of a cross-linking monomer — comprises
 a. at least 80 percent by weight of an hydroxyalkyl ester of acrylic acid or methacrylic acid; or
 b. at least 60 mol percent of acrylamide or methacrylamide or of vinyl pyrrolidone; or
 c. at least 40 mol percent of acrylic acid or methacrylic acid or of their dialkylaminoalkyl esters; or
 d. at least 20 mol percent of water-soluble salts of acrylic acid or methacrylic acid or of salts of quaternization products of dialkylaminoalkyl esters of acrylic acid or methacrylic acid; and
 e. as the balance, comprises water-insoluble monomers.

Water-soluble carrier substances which contain easily-reactable functional groups such as hydroxyl groups or carboxyl groups can, if desired, be modified to any desired degree of cross-linking or swellability by a subsequent reaction with polyfunctional cross-linking agents such as diisocyanates, bis-epoxides, urea-formaldehyde condensates, etc.

A particularly advantageous process for the preparation of water-insoluble carrier substances is described in German Pat. publication No. 2,009,218. According to the process, swellable cross-linked polymers are obtained in the form of pearls about 0.1 – 1 mm diameter, for example, by the polymerization of an aqueous solution of a vinyl monomer and a cross-linking agent in an organic phase. A very high degree of swellability is obtained in these polymers since the polymer is ab initio polymerized in the presence of a large amount of water, i.e., in a swollen condition.

Although the macromolecular substances described above contain groups which are available for a photochemical bonding with polypeptides, it can happen that a sufficient number of bonds between a polypeptide and a carrier will form only after long and intense irradiation. In order to avoid damage to the polypeptide because of over-long irradiation, and to avoid a great expenditure in radiation energy, it has proved useful in these cases to introduce into the carrier substances organic groups which particularly readily undergo a photochemical reaction. Such groups include alkenyl groups in a side chain, particularly those having a terminal double bond, or alkylphenyl groups, among which the toluyl residue is of particular importance. These groups can in many cases be readily introduced by reaction of the carrier substances with toluene-carboxylic acid chloride, toluene sulfochloride, allyl chloride, acrylic acid chloride, and the like. In this manner, the photochemical reactivity of all carrier substances containing hydroxy groups or amino groups, whether they are or are not per se photochemically inert or reactive, can be improved. This is true, for example, of carriers having a polysaccharide structure such as agarose, polydextran, and cellulose, as well as for hydroxyalkyl-substituted polyvinyl compounds such as homopolymers or copolymers of hydroxyalkyl esters or N-hydroxyalkyl amides of acrylic acid or methacrylic acid. When vinyl polymers are used as a carrier, it is more advantageous to incorporate monomers with corresponding side groups directly into their structure, for example vinyl toluene, allyl acrylate, or allyl methacrylate. The amount of such monomers can be from fractions of a percent up to 50 percent or more, calculated on the total weight of the monomers.

In many cases, for example for affinity chromatography of high molecular weight compounds on carrier-bound affinitive proteins, the protein must be at a sufficient distance from the main chain of the carrier polymer. In such cases, carriers having particularly photochemically active groups on longer side chains, e.g., chains having from 6 to 12 carbon atoms, are used. Vinyl polymers comprising units of acrylic or methacrylic acid esters of higher unsaturated alcohols are exemplary of such carriers. Polysaccharides can be modified with corresponding long-chain unsaturated compounds.

In summary, the carrier materials preferred for use in the invention are macromolecules having alkenyl, alkylphenyl, pyrrolidonyl, or imidazolinyl groups outside the main chain thereof or having the structure in the main chain.

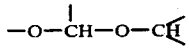

Among the non-polysaccharide carriers, preferred vinyl polymers comprise:

A. 50 to 99 percent by weight of water-soluble vinyl or vinylidene monomer or a mixture of at least 20 mol percent of such a monomer with at most 80 mol percent of a water-insoluble vinyl or vinylidene monomer;

B. 1 to 50 percent by weight of a vinyl or vinylidene monomer wherein the vinyl or vinylidene group is bound to an alkenyl, alkylphenyl, pyrrolidonyl, or imidazolinyl group or to an ester group containing an alkyenyl, alkylphenyl, pyrrolidonyl, or imidazolinyl group in the alcohol portion thereof. These preferred polymers may also comprise C. a cross-linking monomer having at least two carbon-carbon double bonds.

More specifically, such preferred carriers may be vinyl polymers comprising:

A. 50 to 99 percent by weight of acrylic or methacrylic acid, of water-soluble salts of these acids, of hydroxyalkyl esters or dialkylaminoalkyl esters of the acids, of the quaternization products of the aforementioned dialkylaminoalkyl esters, of acrylamide or methacrylamide, or of vinylpyrrolidone, or of mixtures, with water-insoluble vinyl or vinylidene monomers, comprising
1. at least 80 mol percent of an hydroxyalkyl ester of acrylic or methacrylic acid,
2. at least 60 mol percent of acrylamide or methacrylamide or of vinyl pyrrolidone,
3. at least 40 mol percent of acrylic acid or methacrylic acid or of their dialkylaminoalkyl esters,
4. or at least 20 mol percent of water-soluble salts of acrylic or methacrylic acid or of salts or quaternization products of dialkylaminoalkyl esters of these acids;

B. 1 to 50 percent by weight of butadiene, vinyl acrylate and -methacrylate, allyl acrylate and -methacrylate, methallyl acrylate and -methacrylate, of the allyloxy ethyl ester, vinyloxy ethyl ester, toluyloxy ethyl ester, allylamino-hydroxypropyl ester, hexenylamino-hydroxypropyl ester, p-toluenesulfonyloxy ethyl ester, and the imidazolyl ethyl ester of acrylic and -methacrylic acids, of vinyltoluene, vinylpyrrolidone, or of vinylimidazole. Again, such polymers may also comprise C. a cross-linking monomer having at least two carbon-carbon double bonds.

Although polypeptides can be photochemically bonded to one another or cross-linked with one another, polypeptides play no role as carrier substances in the present invention and do not fall within its scope.

The photochemical reaction between the polypeptide and the carrier substance takes place in an aqueous solution of the polypeptide. This term is meant also to encompass solutions of polypeptides in mixtures of water with lower alcohols such as methanol, ethanol, propanol, or butanol, or with acetone, inter alia. The concentration of the polypeptide in the solution employed is suitably in a range from 100 micrograms/ml to 10 milligrams/ml. The carrier substance is generally introduced in such an amount that the polypeptide, on complete binding to the carrier, amounts to from 1 - 50 percent by weight, preferably about 10 percent by weight thereof, although these limits can be exceeded in either direction.

The photochemical reaction itself is preferably initiated by a photosensitizer. Such photosensitizers have long been known in the art. The principles in this field have been reviewed by G. O. Schenck et al. and are, for example, described in R. O. Kan, "Organic Photochemistry", pages 14 - 17, McGraw-Hill, New York (1966).

The term "photosensitization" means the energetic excitement of an acceptor molecule (A) by a donor molecule (D) which primarily absorbs the radiation energy ($h\nu$). In the case under discussion, the sensitizers function as donor molecules, i.e., they are first brought into their lowest excited singlet state ($S_1$) by ultraviolet light, whereafter they convert by intersystem crossing into the lowest triplet state ($T_1$). This state is relatively long-lived and therefore in a condition to convert other molecules into the triplet state by diffusion-controlled energy transmission, from which state these other molecules can react as free radicals. This reaction sequence can be represented as follows:

$$D \xrightarrow{h\nu} D(S_1)$$
$$D(S_1) \rightarrow D(T_1)$$
$$D(T_1) + A \rightarrow D + A(T_1)$$ The acceptor molecule (A) can be either the polypeptide or the carrier molecule, for example.

According to Hammond et al. [J. Am. Chem. Soc. 86, 4537 (1964)], good photosensitizers (donors) should show a high absorption of the irradiation energy and the UV spectrum of the sensitizer (donor) should as much as possible not overlap that of the acceptor and should lie in the long-wave region. Good acceptors further must possess a higher triplet energy than the acceptor and, additionally, exhibit an intersystem crossing which is as efficient as possible. Finally, the photosensitizers should themselves not enter into any photochemical reactions, i.e. should be as inert photochemically as possible. Calvert and Pitts have compiled a number of compounds, using data of Hammond et al. and Ermolaev et al., which are effective as photosensitizers and which are suitable for the process of the present invention [cf. J. G. Calvert and J. N. Pitts, Jr., "Photochemistry", page 298, John Wiley and Sons, Inc., New York (1966), incorporated herein by reference]. Among these, arranged according to decreasing energy of the excited triplet state, are propiophenone, xanthone, acetophenone, triacetyl benzene, isobutyrophenone, diphenylpropanone, benzaldehyde, triphenylmethyl ketone, carbazole, diphenyl oxide, triphenyl amine, dibenzothiophene, o-dibenzoyl benzene, benzophenone, dichlorobenzophenone, diacetyl benzene, fluorene, and many others. Ketones have proved to be particularly effective. In addition to the ketones already mentioned, acetone, methyl ethyl ketone, and metyl isobutyl ketone should be mentioned. Acetophenone and propiophenone are particularly preferred since, because of their absorption spectrum, they absorb a large portion of the energy emitted by a high-pressure mercury lamp, namely in the region of the emission lines at 366 nanometers and at 313 nm.

The photosensitizers particularly useful in the present invention have a triplet energy between about 50 and about 85 kcal/mol. A number of such materials, including and in addition to the materials already mentioned, are tabulated below with their triplet energies.

| Compound | Triplet Energy, $ET_{Kcal/mol}$ Hydrocarbon Solvent |
|---|---|
| Propiophenone | 74.6 |
| Xanthone | 74.2 |
| Acetophenone | 73.6 |
| 1,3,5-Triacetylbenzene | 73.3 |
| Isobutyrophenone | 73.1 |
| 1,3-Diphenyl-2-propanone | 72.2 |
| Benzaldehyde | 71.9 |
| Triphenylmethyl phenyl ketone | 70.8 |
| Carbazole | 70.1 |
| Diphenylene oxide | 70.1 |
| Triphenylamine | 70.1 |
| Dibenzothiophene | 69.7 |
| o-Dibenzoylbenzene | 68.7 |
| Benzophenone | 68.5 |
| 4,4'-Dichlorobenzophenone | 68.0 |
| p-Diacetylbenzene | 67.7 |
| Fluorene | 67.6 |
| 9-Benzoylfluorene | 66.8 |
| Triphenylene | 66.6 |
| p-Cyanobenzophenone | 66.4 |
| Thioxanthone | 65.5 |
| Phenylglyoxal | 62.5 |
| Anthraquinone | 62.4 |
| Phenanthrene | 62.2 |
| α-Naphthoflavone | 62.2 |
| Flavone | 62.0 |
| Ethylphenylglyoxalate | 61.9 |
| 4,4'-Bis(dimethylamino)benzophenone | 61.0 |
| Naphthalene | 60.9 |
| β-Naphthyl phenyl ketone | 59.6 |
| β-Naphthaldehyde | 59.5 |
| β-Acetonaphthone | 59.3 |
| α-Naphthyl phenyl ketone | 57.5 |
| α-Acetonaphthone | 56.4 |
| α-Naphthaldehyde | 56.3 |
| 5,12-Naphthacenequinone | 55.8 |
| Biacetyl | 54.9 |

The excited photosensitizer, by an exchange effect with the polypeptide of the carrier molecule, produces a carbon radical. Typical reactions of this type occur for the glycine group (I) of a polypeptide, for a glucose unit (II) of a polysaccharide, for an acrylamide unit (III) of a vinyl polymer, and for a carrier polymer having a toluyl group (IV), as depicted below, wherein C* designates a carbon radical.

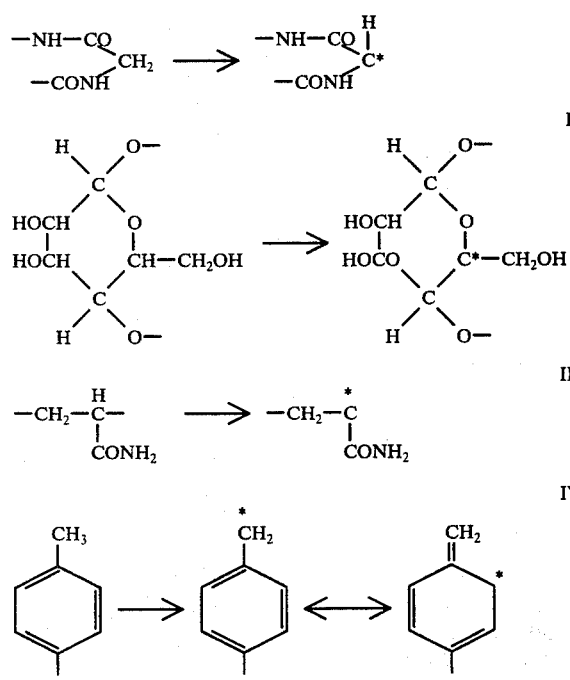

A number of further analogous reactions can occur on other groups of a polypeptide, for example on units of cysteine, cystine, methionine, or tryptophane. Radicals of this type react with one another by recombination, e.g.

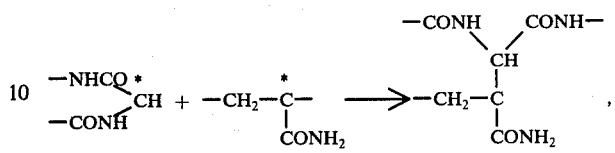

or with olefinic side groups of the carrier polymer by addition and subsequent radical transmission with a particular transmitter (AH), e.g.

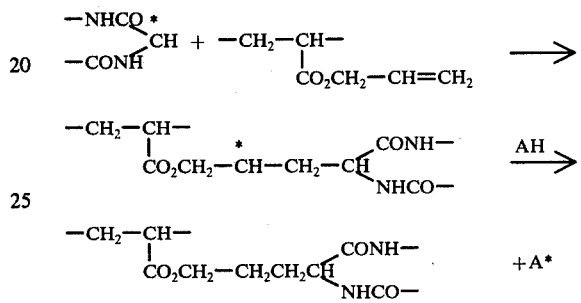

The reactivity of the glycine residue, in preference to other amino acid esters, advantageously affects the process of the present invention since glycine groups are present in almost all natural protein bodies, but are not often important to their function. A photochemical reaction occuring at the glycine group therefore often has no, or only little, influence on the biological activity of the bound polypeptide.

In principle, the initiation of photochemical reactions is not dependent on the presence of a photosensitizer. It is quite possible directly to excite a polypeptide or a carrier molecule by a sufficiently energetic irradiation, i.e., that is to convert it into a free radical. As is known from the work of K. Dose et al., in Photochemistry and Photobiology, 7, 671 – 673 (1968), the direct excitation of polypeptides often leads to inactivation, i.e., the molecular structure is irreversibly disturbed. For best yields, the process of the invention is, therefore, preferably carried out with radiation the energy of which is not sufficient for a direct activation of the polypeptide, but which nevertheless does excite a photosensitizer present. Radiation well suited for the process of the invention is ultraviolet light of a wave length of more than 290 nanometers. Conventional high pressure mercury lamps, in addition to producing radiation in the aforementioned region, also emit stronger radiation in the region of 240 – 280 nanometers. This portion of the radiation is suitably filtered out with "Pyrex" glass.

The period of irradiation depends on the strength of the radiation source and the efficacy of the photosensitizer and can be between ten minutes and 50 hours. When conventional high pressure mercury immersion lamps are employed, i.e., sources having an output of 125 – 500 watts, the radiation times are in general between 1 and 30 hours. After the light source is extinguished, the reaction is immediately ended. Unreacted carrier material, protein, and the protein-carrier compounds are stable and — in contrast to other bonding processes — there is no danger of the hydrolytic cleavage of the photochemically-produced compounds.

The photochemical reaction can also be initiated by irradiation with light in the visible region if, in addition to a photosensitizer excitable by visible light (such as biacetyl), a peroxide such as ditertiary butyl peroxide is employed.

One of the fundamental advantages of the photochemical bonding process in comparison with purely chemical bonding is the free choice of temperature and pH value. The process can be carried out at whatever low temperature is desired and, to the extent the temperature resistance of the polypeptide permits, at whatever high temperature is desired, for example between 5° C. and 70° C. Further, the process can be carried out in a neutral, acid, or alkaline medium. In this way, the process can optimally be chosen to match the stability conditions of the polypeptide. Even the most extremely temperature-sensitive proteins can be worked up under the most protective conditions.

An important prerequisite for the bonding of the polypeptide on a carrier is the absence of oxygen. Oxygen, as is known, is very readily photochemically activated in the presence of sensitizers and initiates a variety of undesired side reactions. Thus, it is necessary to carry out the reaction in an oxygen-free protective gas atmosphere, for example in nitrogen or argon. Also, in order completely to remove oxygen present in the peptide solution, an oxygen-free inert gas is passed therethrough prior to exposure to irradiation.

After conclusion of the irradiation and bonding of the polypeptide on the carrier, the reaction solution may often be used per se for a desired end use. Biologically effective proteins bound to a dissolved carrier can be used, for example, as pharmaceutical preparations of reduced decomposability or resorbability in the body. However, polypeptides bound to soluble carriers can also be recovered in bulk by the addition of precipitating agents, such as inorganic salts or alcohols. The precipitated product can then be filtered and washed with salt solutions or alcohol-water mixtures. Products obtained in solid form can be directly filtered and washed with water.

In the preferred embodiment involving a polypeptide bound to a swellable pearl polymer, the product can be directly dispersed in a substrate solution, whereupon the substrate interacts with the bound polypeptide, for example an enzyme. After reaction of the substrate, the enzyme bound to the carrier can be completely separated by simple filtration. The tightly compacted pearl polymer can be used as filling for a column and the substrate solution can be passed through the column. If a pearl polymer of uniform particle size is employed, a high flow rate can be attained in such a reaction column.

The process of the invention can be realized in a great multiplicity of embodiments which cannot be described exhaustively here. It is self-evident that it is possible to bind different proteins to the same carrier serially or concurrently.

Further embodiments of the invention and their properties will be evident from the following examples, given by way of illustration.

EXAMPLE 1

Acetone-Photosensitized Bonding of Trypsin on Agarose

100 - 200 mesh agarose pearls (commercially available under the tradename "Bio-Gel A-150") were suspended several times in water, washed, and centrifuged. 10 grams of the moist gel so obtained, corresponding with 100 mg of agarose, were suspended in a 90:10 water/acetone mixture containing 50 mg of dissolved trypsin (crystalline 4220 NF/mg). The material was put into a Schenck irradiation apparatus comprising a Pyrex immersion opening, a Pyrex cooling opening, and the reaction vessel. The material was then gassed for 1 hour with oxygen-free nitrogen which was led through 10 percent aqueous acetone. Subsequently, the material was irradiated for 18 hours with good stirring and with water cooling with a high pressure mercury lamp (Philips HPK 125 watt, Model 57203B/00). During the irradiation, the apparatus was wrapped with aluminum foil.

After irradiation, the material was recovered by centrifugation, washed several times with water and 1 N NaCl, and centrifuged.

Protein Determination

The moist gel was washed five more times with water and lyophilized. The nitrogen content was determined by the Kjeldahl method and protein content calculated. Protein content: 21 percent; yield of bound protein: 63 percent.

Enzymatic Activity 5 grams of moist gel were washed several times with 0.05 M phosphate buffer at a pH of 7.5. The moist gel, recovered by centrifugation, was then incubated with 20 ml of a casein substrate solution (4 percent casein, according to Hammarsten, in dilute sodium hydroxide; pH 8.0) with good stirring at 37° C. During the incubation, the pH value was held constant by a glass electrode-controlled automatic burette.

After the enzyme preparation had been re-used three or four times in the same manner, an enzymatic activity of 270 U per 100 mg of dry product, corresponding with 12.9 U per mg of bound protein, was determined. One unit (U) is that amount of enzyme which cleaves one microequivalent of peptide bonds within 60 minutes.

Repeated Use as a Criterion for Covalent Bonding

After use of the material five more times in the above-described manner, no decline in activity was determined. This is an important criterion for the presence of a covalent bonding between trypsin and agarose. Only if activity does not decrease after repeated use with a hydrophilic high molecular weight substrate (in this case casein at pH 8), can one speak of a covalent bonding, since such substrates are most apt to wash out, unspecifically, the protein absorbed on the carrier.

EXAMPLE 2

Acetone-Photosensitized Bonding of Trypsin on Cellulose 1 g of cellulose ("Avicel", microcrystalline 20 - 100 microns) was washed several times with water and irradiated in the manner described in Example 1 in a total volume of 50 ml of a 90:10 water/acetone mixture containing 100 mg of trypsin. The irradiation time was 40 hours.

Working Up

The material was washed with water and 1 N NaCl solution and the product recovered by filtration through a glass frit. Protein content: 4.8 percent; yield of bound protein: 53 percent, calculated on the protein introduced; enzymatic activity per 100 mg of dry product: 27.8 U, corresponding with 5.8 U per mg of bound protein.

After a five-fold repeated use, no decrease in activity was determined.

EXAMPLE 3

Acetone-Photosensitized Bonding of Trypsin on Cellulose Containing Toluyl Groups Cellulose ("Avicel", as in Example 2) was esterified with 4-methyl benzoyl chloride to give a product containing 3.5 percent by weight of toluyl groups.

1 g of this product was washed several times with water and reacted with trypsin in the manner described in Example 2. Irradiation time: 15 hours; protein content: 7.2 percent; yield of bound protein: 83 percent; enzymatic activity per 100 mg of dry product; 49 U, corresponding with 6.9 U per mg of bound protein.

EXAMPLE 4

A. Preparation of a Swellable Acrylamide Pearl Polymer 15 g of acrylamide are polymerized in suspension in the manner described in Example 5A below.

B. Acetone-Photosensitized Bonding of Trypsin to Polyacrylamide Pearls 1 g of polyacrylamide pearls, prepared as above, was swollen in water, washed several times with water, and filtered through a glass frit to give 9.4 g of moist gel.

The total amount of moist gel was reacted with 100 mg of trypsin in the manner described in Example 2 and then washed. Irradiation time: 35 hours; protein content: 6.5 percent (determined by UV spectroscopy after alkaline hydrolysis); yield of bound protein: 73 percent; enzymatic activity/100 mg of dry product: 52.8 U; enzymatic activity/mg of bound protein: 8.1 U.

EXAMPLE 5

A. Preparation of a Swellable Pearl Polymer of Acrylamide and Allyl Methacrylate 87 g of n-heptane and 55 g of perchloroethylene are introduced into a 500 ml round flask equipped with a thermometer, stirrer, reflux condenser, and tube for introducing $CO_2$. 0.25 g of benzoyl peroxide and 0.01 g of a heptane-soluble stabilizer inhibiting polymerization in the heptane phase (commercially available as "4010 Na") are then dissolved therein. After removal of oxygen with about 2 g of dry ice, a monomer solution having the following composition is introduced at 25° C.:

12 g of acrylamide
3 g of allyl methacrylate
0.375 g of glycol dimethacrylate
17.5 g of formamide
0.044 g of a thickening agent (commercially available under the tradename "Plex 4807 F") dissolved in formamide
0.1 g of an emulsifier (statistical copolymer of n-butyl methacrylate: methacryloylcholine chloride, 90:10)

The monomer phase is dispersed in the organic phase by constant stirring. Polymerization is initiated by the addition of 0.25 g of dimethyl aniline. The polymerization takes 8 hours at a temperature below 30° C. with constant introduction of $CO_2$. The fine pearls obtained are freed from the organic phase by decantation and vacuum filtration, are washed in acetone, and dried in vacuum.

By bromine titration, a content of 3.5 percent by weight of allyl methacrylate is determined.

B. Acetone-Photosensitized Bonding of Trypsin on a Pearl Polymer Comprising Acrylamide and Allyl Methacrylate 1 g of the pearl polymer prepared as above was swollen in water, washed several times with water, and filtered to give 9.8 g of moist product.

The total moist product was reacted with 100 mg of trypsin as in Example 4B. Irradiation time: 12 hours; yield of bound protein: 91 percent; protein content: 7.9 percent (determined by UV spectroscopy after alkaline hydrolysis); enzymatic activity/100 mg of dry product; 87 U; enzymatic activity/mg of bound protein: 11 U.

EXAMPLE 6

Acetophenone-Photosensitized Bonding of Different Proteins onto a Pearl Polymer of Acrylamide and Allyl Methacrylate In each case, 2 g of the pearl polymer prepared according to Example 5A were swollen in water to give approximately 20 g of swollen product. In each case, 100 mg of the proteins described below and 80 ml of water saturated with acetophenone at room temperature were added to the swollen pearls. The mixture was then purged for 30 minutes with nitrogen and irradiated for 120 minutes, with continuous nitrogen purging, in the apparatus described in Example 1. Subsequently, the pearls were washed five times with aqueous sodium chloride solution and twice with 0.05 M phosphate buffer (pH = 7.5). The protein content of the product was determined after alkaline hydrolysis (0.5 N NaOH, 6 hours, 95° C.) by the folin method according to Lowry [J. Biol. Chem. 193, 265 (1951)]. Pearls which had been irradiated in the above-described manner in the absence of protein were used as a blind. The yields given are in each case calculated on the amount of protein used.

6(a) Trypsin

Yield of bound protein: 93 percent; protein content: 4.4 percent; enzymatic acitivty; 103 U/100 mg of dry substance; bound protein: 23.4 U/mg.

6(b) α-Chymotrypsin

Yield of bound protein: 88 percent; protein content: 4.3 percent; enzymatic activity: 67 U/100 mg of dry substance; bound protein: 15.6 U/mg.

6(c) Lyophilized pancreatic ribonuclease-A (chromatographically uniform and free of RNase-B, DNase, and protease)

Yield of bound protein: 78 percent; protein content: 3.8 percent; enzymatic activity (pH 7.5, yeast-RNase as substrate, 37° C.): 125 U/100 mg of dry substance; bound protein: 32.8 U/mg (determination of activity by alkalimetric titration as described in Example 1).

6(d) Lyophilized pancreatic α-amylase (320 U/mg)

Yield of bound protein: 85 percent; activity of the bound amylase (starch as a substrate): 60 percent of the activity of the corresponding amount of free amylase.

6(e) Gluco-amylase

The raw enzyme was enriched by precipitation with an ammonium salt and then de-salted by gel filtration on "Sephadex G 25". The product so purified still contained more than 90 percent of foreign protein. The material was reacted photochemically with 20 g of moist pearls per g of protein.

Determination of activity was made with a 30 percent dextran solution prepared from starch by treatment with bacterial amylase. The analysis was effected by gel chromatography on a "Biogel-P2" column according to Dellweg et al., Monatsschrift fuer Brauerei 22, 177 (1969).

In each case, 5 g of moist pearls were shaken overnight with 25 ml of substrate solution. After a 50-fold use, complete substrate decomposition was still observed. Activity of the bound gluco-amylase: 100 percent, calculated on the corresponding amount of free gluco-amylase.

6(f) Trypsin inhibitor according to Kunitz (pancreatic, crystalline, salt-free)

Yield of bound protein: 92 percent.

6(g) Bradykinin

Only 10 mg of bradykinin were employed, which material had been radioactively tagged by the addition of 0.5 microcuries of bradykinin(-tritium). Yield in bound bradykinin: ca. 92 percent (determined by a measure of radioactivity using liquid scintillation counting.)

EXAMPLE 7

Propiophenone-Photosensitized Bonding of Trypsin on a Pearl Polymer Comprising Acrylamide and Allyl Methacrylate Example 6 was repeated with the difference that the aqueous phase contained 5 percent of methanol and 0.005 mol/liter of propiophenone. Yield of bound protein: 96 percent; protein content: 8.1 percent; enzymatic activity/100 mg of dry product: 98 U; enzymatic activity/mg of bound protein: 12.1 U.

EXAMPLE 8

A. Preparation of a Swellable Pearl Polymer of Acrylamide and Glycol Monoacrylate 70 g of n-heptane and 70 g of perchlorethylene are introduced into a 500 ml round flask equipped as in Example 5A. After removal of oxygen by means of 2 g of dry ice, a monomer solution of the following composition is introduced with stirring:
9 g of acrylamide
9 g of 2-hydroxyethylmethacrylate
0.2 g of N,N'-methylene-bis(methacrylamide)
0.9 g of emulsifier (as in Example 5A)
10 g of water
1 g of a 0.1 percent aqueous solution of ammonium peroxy disulfate
1 g of a 0.1 percent aqueous solution of Fe(III) sulfate.

The monomer phase is dispersed in the organic phase by constant stirring. The reaction is initiated by the addition of 0.4 of a 1 percent aqueous sulfurous acid solution. The temperature is maintained at 30° C. during a reaction period of 8 hours. $CO_2$ is introduced during the entire reaction period. The fine pearls obtained are freed from the organic phase by decantation and a short vacuum filtration, washed in water, and dried in vacuum.

B. Acetophenone-Photosensitized Bonding of Trypsin on a Copolymer of Acrylamide and 2-Hydroxyethyl Methacrylate (1:1) Modified with p-Toluyl Sulfochloride The pearl polymer of part A was tosylated to give a produce containing 3.5 percent by weight of toluyl groups and was then reacted with trypsin in the manner described in Example 6 in the presence of acetophenone. Irradiation time: 2 hours, yield of bound protein: 78 percent; protein content: 6.8 percent; enzymatic activity/100 mg of dry product: 84 U; enzymatic activity/mg of bound protein: 12.3 U.

EXAMPLE 9

A. Preparation of a Swellable Pearl Polymer of Acrylamide and Glycol Monomethacrylate A mixture of 14.25 g of acrylamide and 0.75 g of 2-hydroxyethyl methacrylate is polymerized in suspension in the manner described in Example 5A.

B. Acetophenone-Photosensitized Bonding of Trypsin on a Copolymer of Acrylamide with 2-Hydroxyethyl Methacrylamide Modified with 4-Methyl-Phenylacetic Acid Chloride The pearl polymer of part A was converted to a product containing 1.2 percent of toluyl groups by reaction with 4-methyl-phenylacetic acid chloride.

1 gram of the modified product was reacted with trypsin in the manner described in Example 6 in the presence of acetophenone. Irradiation time: 4 hours; yield of bound protein: 85 percent; protein content: 7.4 percent; enzymatic activity/100 mg of dry product: 81.5 U; enzymatic activity/mg of bound trypsin: 11 U.

EXAMPLE 10

A. Preparation of a Water-Soluble Copolymer of Acrylamide and Vinyl Toluene 4.68 g of vinyl toluene and 17.06 g of acrylamide were dissolved in 216 ml of absolute tetrahydrofuran and 0.216 g of azoisobutyric acid dinitrile was added. Air was purged from the reaction vessel with nitrogen. After 2 hours at 65° C., the polymerization was concluded. The precipitation polymer was filtered off, washed several times with tetrahydrofuran, and dried. Yield: 9.58 g; content of toluyl groups: 9 percent by weight (determined by UV-spectroscopy).

The product was dissolved in water and separated into fractions of different molecular weight by gel filtration on "Sephadex G 100". That fraction eluted with the exclusion volume (MW greater than 100000) was lyophilized to give 2.8 g of product.

By gel chromatography of that fraction having a molecular weight below 100000, 530 mg of polymer having a molecular weight of from 5000 – 10000 could be obtained. Namely, that fraction having a molecular weight below 10000 was first obtained by gel filtration on "Sephadex G 50". This fraction was then again gel-filtered on "Sephadex G 25" to obtain that fraction having a molecular weight larger than 5000.

B. Acetophenone-Photosensitized Bonding of Ribonuclease on a Copolymer of Acrylamide and Vinyl Toluene having a Molecular Weight above 100000

500 mg of the soluble polymer prepared in part A and 40 mg of ribonuclease A (chromatographically uniform, 50 U/mg) were dissolved in 50 ml of water saturated with acetophenone and were irradiated as in Example 6 for two hours.

The product was lyophilized and washed with ether to remove traces of acetophenone. An aliquot was dissolved in 0.05 M of phosphate buffer (pH 7.5) and separated on Sephadex G 100. The fractions eluted with the exclusion volume were combined, dialyzed against water, and lyophilized.

The unbound free ribonuclease was also combined, lyophilized, and dissolved in 10 ml of water. Its extinction, measured at 280 nanometers, corresponded with a total amount of 8.5 mg of non-bound ribonuclease. From this, it was determined that 79 percent of the enzyme originally used was bound on the soluble carrier.

Enzymatic activity was determined alkalimetrically in an autotitrator at a pH of 7.5 and 37° C. using yeast nucleic acid (Boehringer) as the substrate. The activity was 35 percent, calculated on the unbound ribonuclease and the ribonuclease content of the carrier.

In a comparison experiment without irradiation, no bonding of ribonuclease to the carrier was found.

C. Acetophenone-Photosensitized Bonding of Insulin on a Copolymer of Acrylamide and Vinyl Toluene having a Molecular Weight from 5000 to 10000

50 ml of water were saturated with acetophenone. 100 mg of insulin and 400 mg of the copolymer prepared in part A having a molecular weight of from 5000 to 10000 were dissolved therein. This solution was combined with 1 ml of 0.1 N hydrochloric acid and irradiated for 2 hours in the manner described in part B. Unbound insulin was separated from insulin bound to the carrier by chromatography on Sephadex G 50. 300 mg of a product having a molecular weight over 10000 and a protein content of 16 percent by weight were obtained. Gel filtration of this product on Sephadex 100 gave a molecular weight greater than 100000 for the major portion of the product.

In a comparison experiment without irradiation, no bonding of insulin to the carrier was found.

EXAMPLE 11

Acetophenone-Photosensitized Bonding of Insulin on Dextran 1000 mg of dextran having a molecular weight of 150000 (commercially available as Dextran 150) and 100 mg of insulin were dissolved in 50 ml of water saturated with acetophenone. The solution was brought to a pH of 4.0 with 0.5 ml of 0.1 N hydrochloric acid.

Irradiation followed as in Examples 10B and C.

By gel filtration on Sephadex G 100, a product having an insulin content of 5.8 percent was obtained, corresponding with a yield of 55 percent calculated on the amount of insulin employed.

EXAMPLE 12

A. Preparation of a Pearl Polymer from Acrylamide and p-Toluyloxy Ethyl Acrylate 174 g of n-heptane and 110 g of perchloroethylene are introduced into a round bottom flask provided with a thermometer, stirrer, reflux condenser, and tube for the introduction of nitrogen. After removal of oxygen by the addition of 2 g of dry ice, a monomer solution is added at 25° C. comprising:

90 parts (13.5 g) of acrylamide
10 parts (1.5 g) of p-toluyloxy ethyl acrylate
1.5 parts (0.225 g) of N,N'-methylene-bis(methacrylamide)
1.33 parts (0.4 g) of the emulsifier of Example 5A
0.66 part (0.1 g) of benzoyl peroxide
70 g of formamide.

The monomer solution is dispersed in the form of droplets in the organic phase by uniform stirring. Polymerization is initiated by the addition of 0.66 part (0.1 g) of dimethyl aniline. The batch fully reacts within three hours, during which nitrogen is introduced and during which a temperature of 30° C. is not exceeded. The pearls obtained are isolated by decantation with acetone and removal of the organic phase by filtration, washing in acetone, and drying in vacuum.

B. Acetophenone-Photosensitized Bonding of γ-Globulin on a Pearl Polymer of Acrylamide and p-Toluyloxy Ethyl Acrylate The pearl polymer of part A (1 g) was swollen in water to form 21.4 g of moist pearls and then irradiated for 120 minutes under a nitrogen atmosphere as in Example 1 in the presence of 100 mg of γ-globulin (7s, human, A grade) in 80 ml of water saturated at room temperature with acetophenone.
Yield of bound protein: 78 percent.

C. Acetophenone-Photosensitized Bonding of Trypsin to a Pearl Polymer of Acrylamide and p-Toluyloxy Ethyl Acrylate Bonding was carried out as in part B only using trypsin instead of γ-globulin. Yield of bound protein: 92 percent; protein content: 8.4 percent; enzymatic activity: 127 U/100 mg of dry substance; bound protein: 15.3 U/mg.

EXAMPLES 13 – 26 (Part A)

The Preparation of Further Pearl Polymers

Proceeding as in Example 12A, further waterswellable carrier polymers were prepared in pearl form changing the nature and amount of the monomers according to the following Table I. The pearls obtained had a diameter of 0.1 – 0.3 mm.

TABLE I

| Example No. | Monomer Mixture | Weight Ratio | Cross-Linking Agent (Parts by Weight per 100 parts of Other Monomers) |
|---|---|---|---|
| 13 | Acrylamide - Vinylacrylate | 70/30 | 0.6 Methylenebis-methacrylamide |
| 14 | Acrylamide - Vinylmethacrylate | 80/20 | 0.6 Methylenebis-methacrylamide |
| 15 | Acrylamide-Allylacrylate-Methylacrylate | 80/20/10 | 0.6 Methylenebis-methacrylamide |
| 16 | Acrylamide-Cyclohexenylaminohydroxypropyl-acrylate | 75/25 | 2 Glycoldimethacrylate |
| 17 | Hydroxyethylacrylate - Allylmethacrylate | 85/15 | 1 Glycoldimethacrylate |
| 18 | Acrylic acid - Allylmethacrylate | 70/30 | 2 Methylolacrylamide |
| 19 | Methacrylic acid - Allylmethacrylate - Ethylmethacrylate | 70/25/5 | 1 Methylenebis-methacrylamide |

TABLE I-continued

| Example No. | Monomer Mixture | Weight Ratio | Cross-Linking Agent (Parts by Weight per 100 parts of Other Monomers) |
|---|---|---|---|
| 20 | Trimethyl(methacryloxyethyl) ammonium chloride - Allylmethacrylate | 60/40 | 3 Methylenebis-methacrylamide |
| 21 | Hydroxyethylacrylate - p -toluene-sulfonoxy ethyl acrylate sulfonoxy ethyl acrylate | 85/15 | 1 Glycoldimethacrylate |
| 22 | Acrylamide - N-vinylpyrrolidone-2 | 80/20 | 2 Methylenebis-methacrylamide |
| 23 | Acrylamide - N-vinylimidazole | 90/10 | 3 Methylenebis-methacrylamide |
| 24 | Acrylamide-2(1-Imidazolyl)-ethyl-methacrylate | 80/20 | 2 Methylenebis-methacrylamide |
| 25 | N-vinylpyrrolidone-2 | 100 | 3 Methylenebis-methacrylamide |
| 26 | Acrylamide - Glycidylacrylate | 80/20 | 0.6 methylenebis-methacrylamide |

EXAMPLES 13 – 26 (Part B)

Acetophenone-Phonosensitized Bonding of Trypsin on the Pearl Polymers of Part A.

In each case, such an amount of the pearl polymers prepared according to Part A was swollen in water as would give 20 g of swollen pearls. The swollen pearl polymer was in each case added to 80 ml of a solution containing 100 mg of trypsin in water that had been saturated at room temperature with acetophenone. The mixture was purged with nitrogen for 30 minutes and, with continuation of the nitrogen purging, irradiated for 120 minutes in the apparatus described in Example 1. Subsequently, the pearls were washed five times with aqueous sodium chloride solution and twice with 0.05 M phosphate buffer (pH = 7.5).

The results are summarized in following Table II.

EXAMPLE 28

A. Chemical Modification of a Pearl Polymer of Acrylamide and Glycidyl Acrylate by Reaction with Allylamine 10 g of the pearl polymer of Example 26 and 20 ml of allylamine were kept at 65° C. for 60 hours and then washed with chloroform. Subsequently, the product was swollen overnight in 0.05 M of phosphate buffer (pH = 7.5) and then washed free of phosphate with water. Yield: 68.2 g of moist product. The content of olefinic double bonds was determined by the bromine addition method to be 4.4 mol percent (calculated on 100 monomer units).

B. Acetophenone-Photosensitized Bonding of Trypsin on the Allylamine-modified Pearl Polymer

TABLE II

| Pearl Polymer | | | | Enzymatic Activity | |
|---|---|---|---|---|---|
| Prepared According to Example No. | Amount Employed (dry weight in g) | Protein Content of the Reaction Product (calculated as dry weight in weight percent) | Yield in Bound Trypsin (calculated on the trypsin introduced-in percent) | Trypsin Units/ 100 mg of Dry Substance | Trypsin Units/ 1 mg of Bound Trypsin |
| 13 | 2.4 | 3.2 | 81 | 64 | 20.0 |
| 14 | 2.7 | 2.8 | 77 | 52 | 18.6 |
| 15 | 3.2 | 2.6 | 85 | 47 | 18.2 |
| 16 | 2.1 | 4.05 | 89 | 85 | 21 |
| 17 | 2.1 | 4.0 | 87 | 89 | 22.3 |
| 18 | 1.5 | 5.7 | 91 | 93 | 16.3 |
| 19 | 3.5 | 2.5 | 90 | 47 | 18.7 |
| 20 | 1.2 | 6.8 | 89 | 36 | 5.3 |
| 21 | 0.8 | 8.3 | 73 | 165 | 19.9 |
| 22 | 1.4 | 4.7 | 73 | 113 | 27 |
| 23 | 3.8 | 1.95 | 76 | 39 | 19.7 |
| 24 | 1.5 | 4.9 | 78 | 107 | 21.8 |
| 25 | 2.0 | 4.05 | 85 | 101 | 22.4 |
| 26 | — | — | — | — | — |

EXAMPLE 27

Acetophenone-Photosensitized Bonding of L-Prolyl-L-Phenylalanyl-Glycyl-L-Lysine-Hydrochloride on a Pearl Polymer of Hydroxyethylacrylate and Allyl Methacrylate 2.1 g of the pearl polymer of Example 17 were swollen in water and gave 20 g of moist pearls. These were combined with 100 mg of the above-mentioned synthetic polypeptide in 80 ml of water which had been saturated at room temperature with acetophenone. The mixture was irradiated as described in Example 6 with the introduction of nitrogen. The polypeptide introduced was bound to an extent of 83 percent.

40 g of the moist pearls and 100 mg of trypsin were irradiated for 60 minutes in the irradiation apparatus described in Example 1 under a nitrogen atmosphere in 60 ml of water saturated at room temperature with acetophenone. Yield of bound protein: 83 percent; protein content: 1.38 percent; enzymatic activity: 23 U/100 mg of dry product; bound protein: 16.7 U/mg.

EXAMPLE 29

2-Acetyl Benzoate-Photosensitized Bonding of Trypsin on a Pearl Polymer of Acrylamide and Allyl Methacrylate Irradiation was carried out as in Example 6 with the difference that 80 ml of a 0.01 M sodium-2-acetyl benzoate solution (pH = 7.5) was employed instead of water saturated with acetophenone. Yield of bound protein: 89 percent; protein content: 4.2 percent; enzymatic activity: 98 U/100 mg of dry substance; bound protein: 23.4 U/mg.

EXAMPLE 30

Benzophenone-Photosensitized Bonding of Trypsin on a Pearl Polymer of Acrylamide and Allyl Methacrylate Irradiation was carried out as in Example 6 with the difference that 80 ml of a 0.005 M solution of benzophenone in water/methanol (90/10) was used. The irradiation time was 60 minutes. Yield of bound protein: 85 percent; protein content: 4.06 percent; enzymatic activity: 104 U/100 mg of dry substance; bound protein: 25.5 U/mg.

EXAMPLE 31

Benzophenone-2-Carboxylic Acid-Photosensitized Bonding of Trypsin on a Pearl Polymer of Acrylamide and Allyl Methacrylate Irradiation was carried out as in Example 6 with the difference that 80 ml of a 0.01 M solution of benzophenone-2-carboxylic acid in 0.01 N NaOH was used. Yield of bound protein: 75 percent; protein content: 3.6 percent; enzymatic activity: 102 U/100 mg of dry substance; bound protein: 28 U/mg.

EXAMPLE 32

Acetophenone-Photosensitized Bonding of α-Chymotrypsin on a Copolymer of Butadiene and Acrylamide

A. Preparation of a Copolymer of Butadiene and Acrylamide

Acrylamide (0.75 mol) and butadiene (0.5 mol) were polymerized in ethylene glycol (125 ml) at 60° C. in an autoclave using potassium persulfate as an initiator. After degassing and washing in n-butanol and drying, a resinous brittle product was obtained which was mechanically subdivided into particles from about 0.100 mm to 0.200 mm diameter.

1 g of the product swelled in water to give 19 g of moist product.

The swollen product is water-insoluble and has the nature of a colorless hydrophilic gel. It contains 6 mol percent of olefinic double bonds as determined by bromine addition.

B. Acetophenone-Sensitized Bonding of α-Chymotrypsin 40 g of the moist gel of Part A and 100 mg of α-chymotrypsin in 60 ml of water saturated with acetophenone at room temperature were irradiated for 60 minutes, while being purged with nitrogen, in the apparatus more fully described in Example 1. Yield of bound protein: 88 percent; protein content: ca. 4 percent; enzymatic activity: 63 U/100 mg of dry substance; bound protein: 15.7 U/mg.

EXAMPLE 33

Photochemical Bonding of Trypsin on a Pearl Polymer of Acrylamide and Allyl Methacrylate using Ultraviolet Light having a Wave Length greater than 300 Nanometers, in the Absence of a Photosensitizer The irradiation was carried out in the same manner as in Example 6 with the difference that no acetophenone was present. Yield of bound protein: 57 percent; protein content: 2.8 percent; enzymatic activity: 58 U/100 mg of dry substance; bound protein: 17.2 U/mg.

EXAMPLE 34

Photochemical Bonding of Ribonuclease-A on a Pearl Polymer of Acrylamide and p-Tolueneoxy Ethyl Acrylate Using Visible Light in the Presence of Biacetyl and Di-t-butyl peroxode 1 g of the pearl polymer of Example 12 was swollen in water and produced about 21 g of swollen pearls.

20 g of the swollen pearls, 100 mg of pancreatic ribonuclease-A, and 80 ml of methanol/water (20/80) containing 0.5 mg biacetyl/ml and 1 mg di-t-butyl peroxide/ml were irradiated, with nitrogen purging, with a HPR-125 watt Philips daylight lamp through a filter which absorbed light of wave lengths shorter than 385 nanometers. Irradiation was carried out for 240 minutes.

The product was washed three times with methanol/water (30/70), five times with aqueous sodium chloride solution, and twice with 0.05 M phosphate buffer (pH = 7.5). Yield of bound protein: 39 percent; protein content: 3.7 percent; enzymatic activity: 41 U/100 mg of dry substance; bound protein: 11 U/mg.

EXAMPLE 35

A. Preparation of an Emulsion Polymer of Methylmethacrylate and Allyl Methacrylate 320 g of water, 0.24 g of sodium lauryl sulfate, and 0.16 g of ammonium persulfate were heated to 80° C. in a vessel equipped with a stirrer. A mixture of 960 g of water, 0.768 g of sodium lauryl sulfate, 2.16 g of ammonium persulfate, 288 g of methylmethacrylate, and 44.8 g of allyl methacrylate was added to the vessel over a period of four hours. After polymerizing to completion for a further two hours at 80° C., the vessel was cooled to room temperature.

B. Photochemical Bonding of Ribonuclease-A 80 ml of water saturated with acetophenone, 0.16 g of sodium lauryl sulfate, and 100 mg of ribonuclease-A were added to 20 ml of the dispersion of Part A and the mixture was irradiated for 60 minutes in the apparatus described in Example 1.

The mixture was then centrifuged at 10000 G. The supernatant liquid was drawn off and the centrifugate was shaken with 0.2 percent of aqueous sodium lauryl sulfate solution and again centrifuged. This process was repeated 10 times. By determination of nitrogen according to the Kjeldahl method, a yield of 98 percent of bound protein was determined. Enzymatic activity of the bound RNase (37° C., yeast-RNA, pH = 7.5): 100 percent, compared with free RNase.

In a control experiment (dispersion + RNase without irradiation), neither RNase nor enzymatic activity could be found in the dispersion.

What is claimed is:

1. A method for bonding a polypeptide to a macromolecular carrier which comprises irradiating an aqueous solution of a polypeptide, in the absence of oxygen and in the presence of a macromolecular carrier compound having a molecular weight of at least 1000, with ultraviolet light in the presence or absence of a photosensitizer, or with visible light in the presence of a photosensitizer and of an organic peroxide, wherein said macromolecular carrier compound is (a) a non-cross-linked water-soluble compound, (b) a cross-linked compound swellable in water to at least twice its dry volume, or (c) a cross-linked or non-cross-linked compound non-swellable in water or swellable to less than twice its dry volume and comprises latex particles having a diameter of at most 1 micron, said macromolecular carrier compound further being a polymer which is A. a polymer of at least one monomer selected from the group consisting of acrylic acid, methacrylic acid, the amides of these acids, the water-soluble salts of these acids, the hydroxy alkyl esters of these acids, the dialkyl aminoalkyl esters of these acids, and the water-soluble salts and quaternization products of the dialkyl aminoalkyl esters of these acids, B. a copolymer of at least one monomer of (A) with at least one vinyl or vinylidene monomer readily undergoing a photochemical reaction and having a vinyl or vinylidene group bound to an alkenyl, alkylphenyl, pyrrolidonyl, or imidazolinyl group, or bound to an ester group or a substituted amido group wherein an alkenyl, alkylphenyl, pyrrolidonyl, or imidazolinyl group is present in the alcohol portion of said ester group or in the substituent on said amido group, or C. a polymer of (A) or (B) which additionally comprises a water-insoluble vinyl or vinylidene monomer different from those readily undergoing a photochemical reaction mentioned in (B) above.

2. A method as in claim 1 wherein said polymer comprises from 50 to 99 percent by weight thereof of at least one monomer (A), alone or in a mixture containing up to 80 percent by weight of a water-insoluble vinyl or vinylidene monomer not readily undergoing a photochemical reaction, and 50 to 1 percent by weight of a vinyl or vinylidene monomer readily undergoing a photochemical reaction and having a vinyl or vinylidene group bound to an alkenyl, alkylphenyl, pyrrolidonyl, or imidazolinyl group, or bound to an ester group or substituted amido group wherein an alkenyl, alkylphenyl, pyrrolidonyl, or imidazolinyl group is present in the alcohol portion of said ester group or in the substituent on said amido group.

3. A method as in claim 1 wherein said polymer is cross-linked by the presence therein of a monomer having at least two polymerizable carbon-carbon double bonds.

4. A method as in claim 2 wherein said polymer is a polymer formed from a monomer mixture comprising, as monomer (A),
   i. at least 80 mol percent of an hydroxyalkyl ester of acrylic acid or methacrylic acid; or
   ii. at least 60 mol percent of acrylamide or methacrylamide; or
   iii. at least 40 mol percent of acrylic acid, methacrylic acid, or of a dialkyl aminoalkyl ester of these acids; or
   iv. at least 20 mol percent of a water-soluble salt of acrylic acid or methacrylic acid or of a water-soluble salt or quaternization product of a dialkyl aminoalkyl ester of these acids, the balance of the mixture, exclusive of those monomers readily undergoing a photochemical reaction, in each case being a water-insoluble vinyl or vinylidene monomer different from those readily undergoing a photochemical reaction mentioned in claim 1.

5. A method as in claim 1 wherin said polymer is a polymer comprising, as said monomer readily undergoing a photochemical reaction, a vinyl or vinylidene monomer having a vinyl or vinylidene group bound to an alkenyl, alkylphenyl, pyrrolidonyl, or imidazolinyl group, or bound to an ester group or a substituted amido group wherein an alkenyl, alkylphenyl, pyrrolidonyl, or imidazolinyl group is present in the alcohol portion of said ester group or in the substituent on said amido group, which monomer is selected from the group consisting of butadiene, vinyl acrylate, vinyl methacrylate, allyl acrylate, allyl methacrylate, methallyl acrylate, methallyl methacrylate, vinyl toluene, vinyl pyrrolidone, vinyl imidazole, and the allyloxy ethyl esters, vinyloxy ethyl esters, toluyloxy ethyl esters, allylaminohydroxypropyl esters, hexenyl-aminohydroxypropyl esters, p-toluene-sulfonyl-oxyethyl esters, and imidazolyl-ethyl esters of acrylic acid and methacrylic acid.

6. A method as in claim 1 wherein said polymer comprises
   i. 50 – 99 percent by weight thereof of acrylamide or methacrylamide and
   ii. 50 – 1 percent by weight of allyl acrylate or allyl methacrylate.

7. A method as in claim 4 wherein said polymer comprises
   i. 50 – 99 percent by weight thereof of a monomer mixture comprising at least 60 percent by weight of acrylamide or methacrylamide, the balance of said mixture being a water-insoluble vinyl or vinylidene monomer different from those readily undergoing a photochemical reaction mentioned in claim 4, and, as said monomer readily undergoing a photochemical reaction,
   ii. 50 – 1 percent by weight of allyl acrylate or allyl methacrylate.

8. A method as in claim 1 wherein said solution is irradiated with ultraviolet or visible light in the presence of a photosensitizer having a triplet energy between about 50 and about 85 kcal per mol.

9. A method for bonding a polypeptide to a carrier which is a cross-linked pearl copolymer of acrylamide and allyl methacrylate having a molecular of at least 1000, which method comprises irradiating an aqueous solution of a polypeptide, in the absence of oxygen and in the presence of said carrier, with ultraviolet light in the presence or absence of a photosensitizer or, in the presence of a photosensitizer and of an organic peroxide, with visible light.

* * * * *